United States Patent
Akashi et al.

(10) Patent No.: US 6,387,414 B1
(45) Date of Patent: May 14, 2002

(54) METHOD FOR PREPARING HYDROXYAPATITE COMPOSITE AND BIOCOMPATIBLE MATERIAL

(75) Inventors: Mitsuru Akashi, 2-14-6, Kotokujidai, Kagoshima-shi, Kagoshima-ken 891-0103; Tetsushi Taguchi, Tsukuba; Akio Kishida, Kagoshima; Akio Hayashi, Kashiwa, all of (JP)

(73) Assignees: NOF Corporation, Tokyo; Mitsuru Akashi, Kagoshima, both of (JP)

( * ) Notice: Subject to any disclaimer, the term of this patent is extended or adjusted under 35 U.S.C. 154(b) by 0 days.

(21) Appl. No.: 09/368,960

(22) Filed: Aug. 5, 1999

(51) Int. Cl.$^7$ .......................... A61K 33/42; A61K 9/00; A61K 33/06; A61K 47/30
(52) U.S. Cl. ...................... 424/602; 424/484; 424/485; 424/486; 424/487; 424/488; 424/601; 424/682; 514/772.1; 514/772.2; 514/772.3; 514/772.4; 514/772.5; 514/772.6; 514/772.7; 514/773; 514/777; 514/781; 514/788.1
(58) Field of Search .................................. 424/601, 602, 424/603, 682, 484, 485, 486, 487, 488; 514/772.1, 772.2, 772.3, 772.4, 772.5, 772.6, 772.7, 773, 777, 781, 788.1

(56) References Cited

FOREIGN PATENT DOCUMENTS

JP         2000327314     * 11/2000

OTHER PUBLICATIONS

STN/CAS online, file JICST–EPlus, Acc. No. 990809595, (Shiraogawa et al., 'An apatite formation on surface treated polymer films by an alternate soaking process', Kobunshi Gakkai Yokoshu (Polymer Preprints, Japan) (1999), vol. 48, No. 3, p. 500), Abstract.*

Taguchi et al., 'Hydroxyapatite formation on/in poly(vinyl alcohol) hydrogel matrices using a novel alternate soaking process', Chemistry Letters (1998), pp. 711, 712.*

Kulik et al., 'In vitro platelet adhesion to nonionic and ionic hydrogels with different water contents', Journal of Bimedical Materials Research, vol. 30, pp. 295–304.*

STN/CAS online, file CAPLUS, Acc. No. 1998:25343, Doc. No. 128:93241, (Mizushima et al., JP 10001375 (1998), Abstract.*

STN/CAS online, file CAPLUS, Acc. No. 2000:47374, Doc. No. 132:339249, (Taguchi et al., Bioceram., Proc. Int. Symp. Ceram. Med. (1999), 12, pp. 133–136), Abstract.*

* cited by examiner

Primary Examiner—Jose' G. Dees
Assistant Examiner—Frank Choi
(74) Attorney, Agent, or Firm—Darby & Darby

(57) ABSTRACT

A method for preparing a hydroxyapatite composite is disclosed. This method comprises alternately soaking a matrix which has been made hydrophilic at least on its surface, in a calcium ion aqueous solution containing calcium ions and substantially free of phosphate ions and in a phosphate ion aqueous solution containing phosphate ions and substantially free of calcium ions to securely form hydroxyapatite at least on the surface of the matrix. Also disclosed is a biocompatible material composed of the hydroxyapatite composite obtained by the method.

12 Claims, 2 Drawing Sheets

METHOD FOR PREPARING HYDROXYAPATITE COMPOSITE AND BIOCOMPATIBLE MATERIAL

FIELD OF THE INVENTION

The present invention relates to a method for preparing a hydroxyapatite composite that has a composition similar to that of bone, and that is useful as various kinds of artificial tissues for living organisms such as artificial bone, as well as medical materials. The present invention also relates to a biocompatible material utilizing the composite obtained by the above method.

DESCRIPTION OF RELATED ART

Natural bone and teeth are molecular composites of inorganic hydroxyapatite (HAp) and collagen, arranged in a three-dimensional matrix. For repairing damaged bone and teeth, it is known to use biocompatible ceramics. Examples of such ceramics include "Bioglass" (trade name, manufactured by NIPPON ELECTRIC GLASS CO., LTD., OTSU. SIGA, JAPAN) composed of $Na_2O$—$CaO$—$SiO_2$—$P_2O_5$ and mainly used as a restorative materials in dental surgery, sintered HAp ($Ca_{10}(PO_4)_6(OH)_2$) mainly used as a bone filling material, and crystallized glass containing apatite and wollastonite ($CaO$—$SiO_2$) (trade name "Cerabone A-W" manufactured by NIPPON ELECTRIC GLASS CO., LTD., OTSU SIGA, JAPAN) used for an artificial otoconite or an ilium spacer.

There has been an attempt to have such ceramics formed on the surface of a matrix having high strength, such as a metal matrix, for use as a substitute for natural bone. Also, in an attempt to produce a flexible, durable material that can be used as artificial tissue for living organisms other than bone, there has been developed a so-called biomimetic process, a method for forming HAp on the surface of readily processible polymer matrices.

The biomimetic process includes the steps of introducing glass particles composed mainly of $CaO$ and $SiO_2$ in an aqueous solution having the ion concentration equivalent to that of human body fluid (simulated body fluid), soaking a polymer matrix in the simulated body fluid to have a number of apatite nuclei formed on the surface of the polymer matrix, and then soaking the matrix in an aqueous solution having the ion concentration 1.5 times that of the simulated body fluid for reaction. It has been reported that according to the biomimetic process, the apatite nuclei grow on the polymer matrix, and a compact and homogeneous bone-like HAp layer is formed with an intended thickness (J.Biomed.Mater.Res.Vol.29, p349–357(1995)).

In the biomimetic process, however, the growth speed of HAp is so slow that even the reaction for as long as more than two weeks cannot generate sufficient amount of HAp on the polymer matrix for use as artificial bone.

As a new method for hydroxyapatite synthesis, there has been proposed alternate soaking process wherein a matrix is soaked in a calcium ion aqueous solution and subsequently in a phosphate ion aqueous solution, and this alternate soaking cycle is repeated to gradually form HAp.

When the alternate soaking process is used for forming HAp on a general-purpose polymer matrix such as of polyethylene, nylon, or silicone, the resulting HAp is mostly amorphous, with a small portion of crystalline HAp. In addition, the bonding strength of the obtained HAp to the polymer matrix is sometimes insufficient.

It is believed that formation of bone-like structures requires the steps of (a) adsorption of inorganic ions by polymer chains, (b) formation of initial HAp crystals as nuclei, (c) formation of HAp layers, and (d) formation of molecular polymer composites. In the alternate soaking process using a general-purpose polymer matrix, the step (b) may be achieved relatively easily, but it is difficult to proceed with the process beyond this step.

DISCLOSURE OF THE INVENTION

It is an object of the present invention to provide a method for preparing a HAp composite having the composition and crystal structure similar to those of natural bone, and expected to have superior affinity, which method enables extremely rapid and efficient formation of HAp on a polymer or metal matrix with excellent bonding strength therebetween.

It is another object of the present invention to provide a biocompatible material that has HAp having the composition and structure similar to those of natural bone, that is expected to have superior affinity, and that has excellent bonding strength between the HAp and the matrix.

According to the present invention, there is provided a method for preparing a hydroxyapatite composite comprising alternately soaking a matrix which has been made hydrophilic at least on its surface (sometimes referred to as matrix (C) hereinbelow), in a calcium ion aqueous solution containing calcium ions and substantially free of phosphate ions (sometimes referred to as calcium ion aqueous solution (A) hereinbelow) and in a phosphate ion aqueous solution containing phosphate ions and substantially free of calcium ions (sometimes referred to as phosphate ion aqueous solution (B) hereinbelow) to securely form hydroxyapatite at least on the surface of the said matrix.

According to the present invention, there is also provided the above method further comprising, after soaking the matrix (C) in the calcium ion aqueous solution (A), removing the calcium ion aqueous solution (A) remaining on the matrix (C) before soaking the matrix (C) in the phosphate ion aqueous solution (B)

According to the present invention, there is also provided the above method further comprising, after soaking the matrix (C) in the phosphate ion aqueous solution (B), removing the phosphate ion aqueous solution (B) remaining on the matrix (C) before soaking the matrix (C) in the calcium ion aqueous solution (A).

According to the present invention, there is further provided a biocompatible material consisting essentially of a hydroxyapatite composite prepared in accordance with the above method.

PREFERRED EMBODIMENTS OF THE INVENTION

Figure 1:
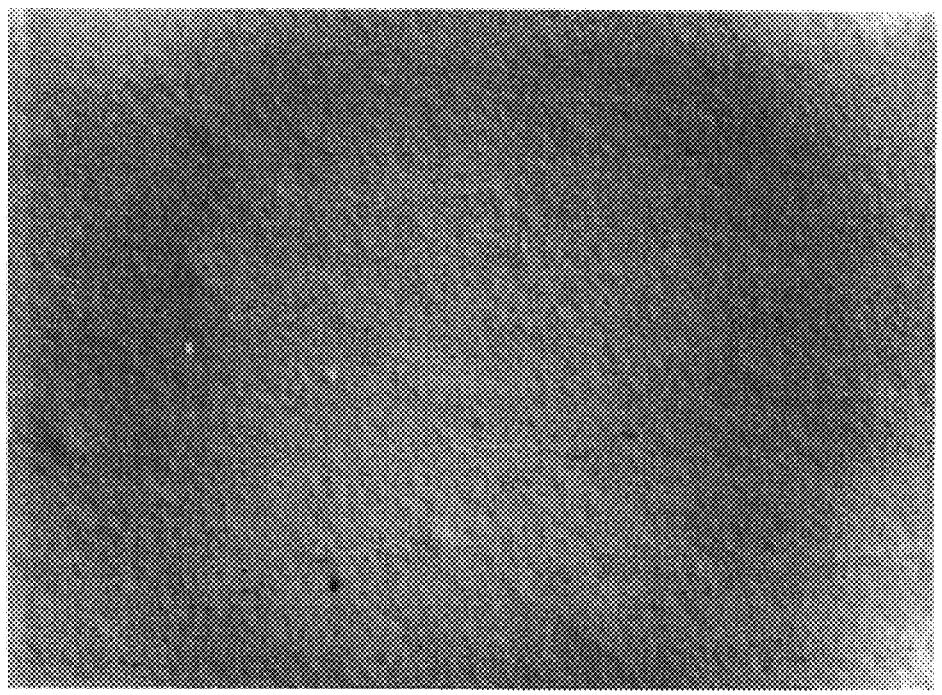
FIG. 1 is a SEM micrograph of the HAp of the HAp composite prepared in Comparative Example 2.

The present invention will now be explained in detail.

The method for preparing a HAp composite of the present invention includes the step of alternately soaking matrix (C) in calcium ion aqueous solution (A) and in phosphate ion aqueous solution (B) to securely form hydroxyapatite at least on the surface of the matrix (C).

The calcium ion aqueous solution (A) contains calcium ions, and is substantially free of phosphate ions. Presence of phosphate ions in the calcium ion aqueous solution (A) may reduce the speed of HAp formation, so that the calcium ion aqueous solution (A) is usually an aqueous solution that contains calcium ions but no phosphate ions. Examples of the calcium ion aqueous solution (A) may include an aqueous solution of calcium chloride, an aqueous solution of calcium acetate, a tris buffer solution of calcium chloride, a tris buffer solution of calcium acetate, and mixtures thereof.

The calcium ion concentration in the calcium ion aqueous solution (A) is preferably 0.01 to 10 mol/L, more preferably 0.1 to 1 mol/L, taking the speed and efficiency of HAp formation into account. The pH of the calcium ion aqueous solution (A) is not particularly limited. When a tris buffer solution is used, the pH of the calcium ion aqueous solution (A) is preferably 6 to 10, more preferably 7.4.

The phosphate ion aqueous solution (B) contains phosphate ions, and is substantially free of calcium ions. Presence of calcium ions in the phosphate ion aqueous solution (B) may reduce the speed of HAp formation, so that the phosphate ion aqueous solution (B) is usually an aqueous solution that contains phosphate ions but no calcium ions. Examples of the phosphate ion aqueous solution (B) may include an aqueous solution of sodium hydrogenphosphate, an aqueous solution of sodium dihydrogenphosphate, an aqueous solution of ammonium dihydrogenphosphate, a tris buffer solution of sodium hydrogenphosphate, a tris buffer solution of sodium dihydrogenphosphate, a tris buffer solution of ammonium dihydrogenphosphate, and mixtures thereof.

The phosphate ion concentration in the phosphate ion aqueous solution (B) is preferably 0.01 to 10 mol/L, more preferably 0.1 to 1 mol/L, taking the speed and efficiency of HAp formation into account. The pH of the phosphate ion aqueous solution (B) is not particularly limited. When a tris buffer solution is used, the pH of the phosphate ion aqueous solution (B) is preferably 6 to 10, more preferably 7.4.

Any combinations of the calcium ion aqueous solution (A) and the phosphate ion aqueous solution (B) may be employed. For example, combination of an aqueous solution of calcium chloride and an aqueous solution of sodium hydrogenphosphate, an aqueous solution of calcium acetate and an aqueous solution of sodium dihydrogenphosphate, or an aqueous solution of calcium acetate and an aqueous solution of ammonium dihydrogenphosphate may be used.

The calcium ion aqueous solution (A) and the phosphate ion aqueous solution (B) may contain other ions as long as the desired objects of the present invention are achieved. When 2.5 mM or more of magnesium ions ($Mg^{2+}$) is contained in the solution (A). and/or (B), however, tricalcium phosphate (TCP) may be formed, thus not being preferred.

The matrix (C) used in the present method is a matrix that has been made hydrophilic at least on its surface. For example, the matrix (C) may be made from a polymer, and may have on its surface hydrophilic groups such as carbonyl groups, esters, carboxyl groups, phosphoric acid groups, sulfonic acid groups, or hydroxyl groups. In the method of the present invention utilizing the alternate soaking process, the matrix (C) made from a polymer matrix preferably has at least one of carboxyl, phosphoric acid, and sulfonic acid groups as the hydrophilic groups in order to form compact, crystalline HAp. "A matrix which has been made hydrophilic at least on its surface" means that the matrix has been made hydrophilic on a part or all of its surface, and may optionally been made hydrophilic inside thereof.

The matrix (C) may be prepared, for example, by subjecting a polymer matrix to corona treatment, plasma treatment, acid treatment, base treatment, or surface filing, or by subjecting a metal matrix to acid treatment on its surface or surface filing. Two or more of such corona treatment, plasma treatment, acid treatment, base treatment, and surface filing may be combined to prepare the matrix (C).

The polymer matrix as a starting material for the matrix (C) may be made of, for example, polyurethane, polyethylene, polypropylene, polylactic acid poly (glycolic acid), polyester, polyamide, polycarbonate, a fluoropolymer (such as Teflon (trademark)), a silicon elastomer, polyvinyl alcohol, polyethylene glycol, poly-γ-glutamic acid, collagen, glucosylethyl methacrylate (GEMA), partially sulfated GEMA, a mucopolysaccharide (such as hyaluronic acid), cellulose, chitin, chitosan, pullulan, or fibronectin.

The metal matrix as an alternative starting material for the matrix (C) may be made of, for example, titanium or stainless steel.

The corona treatment, plasma treatment, acid treatment or base treatment may be carried out by a known method, and the conditions for the treatment are not particularly limited as long as the surface of the matrix is made hydrophilic. The kind of the acid or the base may suitably be selected. The surface filing may be carried out with a file or an abrasive, as long as fine irregularities or scratches are formed on the matrix surface to make the matrix surface hydrophilic.

Alternatively, the matrix (C) may be prepared by subjecting a polymer matrix to at least one of the treatments mentioned above, and then graft-polymerizing a hydrophilic polymerizable compound to the surface of the treated matrix, or effecting reaction of a hydrophilic polymer with the surface of the treated matrix.

The hydrophilic polymerizable compound to be graft-polymerized to the polymer matrix surface and the hydrophilic polymer to be reacted with the polymer matrix surface are not particularly limited as long as the compound and the polymer have hydrophilic groups such as carboxyl groups, phosphoric acid groups, or sulfonic acid groups. Examples of the hydrophilic polymerizable compound may include (meth)acrylic acid, alkyl ester of (meth)acrylic acid, alkylamide of (meth)acrylic acid, (meth)acrylic acid having a urethane bond, (meth)acrylic acid having a urea bond, (meth)acrylic acid having a phosphoric acid group, (meth)acrylic acid having a sulfonic acid group, and oligomers having one of these compounds as a unit. Examples of the hydrophilic polymer may include those having one of the above compounds as a unit.

The graft-polymerization may be effected by an ordinary grafting method, and the amount of grafts is not particularly limited. In order to form larger amount of crystalline HAp, however, a certain amount of grafts is desired. Particularly suitable amount of the grafts is 23 to 43 $\mu g/cm^2$ more, preferably about 30 $\mu g/cm^2$. When the amount of grafts is in the range of 10 to 33 $\mu g/cm^2$, HAp crystals in the form of flakes prevail, whereas when the amount of grafts exceeds this range, HAp crystals in the form of plates are observed.

The molecular weight of the polymer used for the matrix (C) is not particularly limited. In addition, the matrix (C) are not particularly limited in shape, and may be in the form of a plate, a film, a membrane, a cylinder, meshes, or fibers.

According to the present invention, the matrix (C) may be soaked in the calcium ion aqueous solution (A) and in the phosphate ion aqueous solution (B) by: (1) carrying out one or more cycles of soaking the matrix (C) in the calcium ion aqueous solution (A) and then in the phosphate ion aqueous solution (B), or (2) carrying out one or more cycles of soaking the matrix (C) in the phosphate ion aqueous solution (B) and then in the calcium ion aqueous solution (A).

By increasing the number of cycles, the amount of HAp formed on the matrix may be increased. The number of cycles is usually 1 to 200, preferably 5 to 100. When the cycle of the operations is repeated, the method (1) mentioned above does not necessarily terminate with the soaking of the matrix (C) in the phosphate ion aqueous solution (B), but may terminate with the soaking in the calcium ion aqueous solution (A). Similarly, the method (2) does 1 not necessarily terminate with the soaking of the matrix (C) in the calcium ion aqueous solution (A), but may terminate with the soaking in the phosphate ion aqueous solution (B).

For formation of still stronger bond between the resulting HAp and the matrix (C), the matrix (C) for method (1) mentioned above is preferably a matrix having on its surface at least one of carboxyl, phosphoric acid, and sulfonic acid groups, which are capable of forming ion complex with calcium ions, whereas for method (2), a matrix having on its surface groups that are capable of forming ion complex with phosphate ions.

The duration of the soaking of the matrix (C) in the calcium ion aqueous solution (A) may suitably be selected depending on the speed and efficiency of HAp formation. The total duration of the soaking in the calcium ion aqueous solution (A) is usually 10 minutes to 168 hours, preferably 30 minutes to 72 hours, more preferably 1 hour to 24 hours. Similarly, the duration of the soaking of the matrix (C) in the phosphate ion aqueous solution (B) may also be selected suitably depending on the speed and efficiency of HAp formation. The total duration of the soaking in the phosphate ion aqueous solution (B) is usually 10 minutes to 168 hours, preferably 30 minutes to 72 hours, more preferably 1 hour to 24 hours. The duration of each operation of soaking the matrix (C) in the calcium ion aqueous solution (A) or in the phosphate ion aqueous solution (B), when the cycle of the operations is repeated, may suitably be selected, taking the preferred total duration of the soaking into account. For example, each soaking may be for about 10 seconds.

The temperature of the solutions in which the matrix (C) is soaked may suitably be selected, taking the speed and efficiency of HAp formation into account. The temperature of the solutions is usually 0 to 90° C., preferably 4 to 80° C.

In the method of the present invention, it is preferred, following the soaking of the matrix (C) in the calcium ion aqueous solution (A) to remove the calcium ion aqueous solution (A) remaining on the matrix (C) before the matrix (C) is soaked in the phosphate ion aqueous solution (B), and/or, following the soaking of the matrix (C) in the phosphate ion aqueous solution (B), to remove the phosphate ion aqueous solution (B) remaining on the matrix (C) before the matrix is soaked in the calcium ion aqueous solution (A).

The removal of the calcium ion aqueous solution (A) or the phosphate ion aqueous solution (B) remaining on the matrix (C) may be carried out by any method as long as the calcium ions or phosphate ions remaining on the surface of the matrix (C) are eliminated. For example, the matrix (C) may be washed with a liquid, such as water, that can eliminate the ions. It is preferred to dry the washed matrix (C) by air drying, or by soaking the washed matrix (C) in a volatile liquid such as acetone, followed by air-drying.

Figure 3:
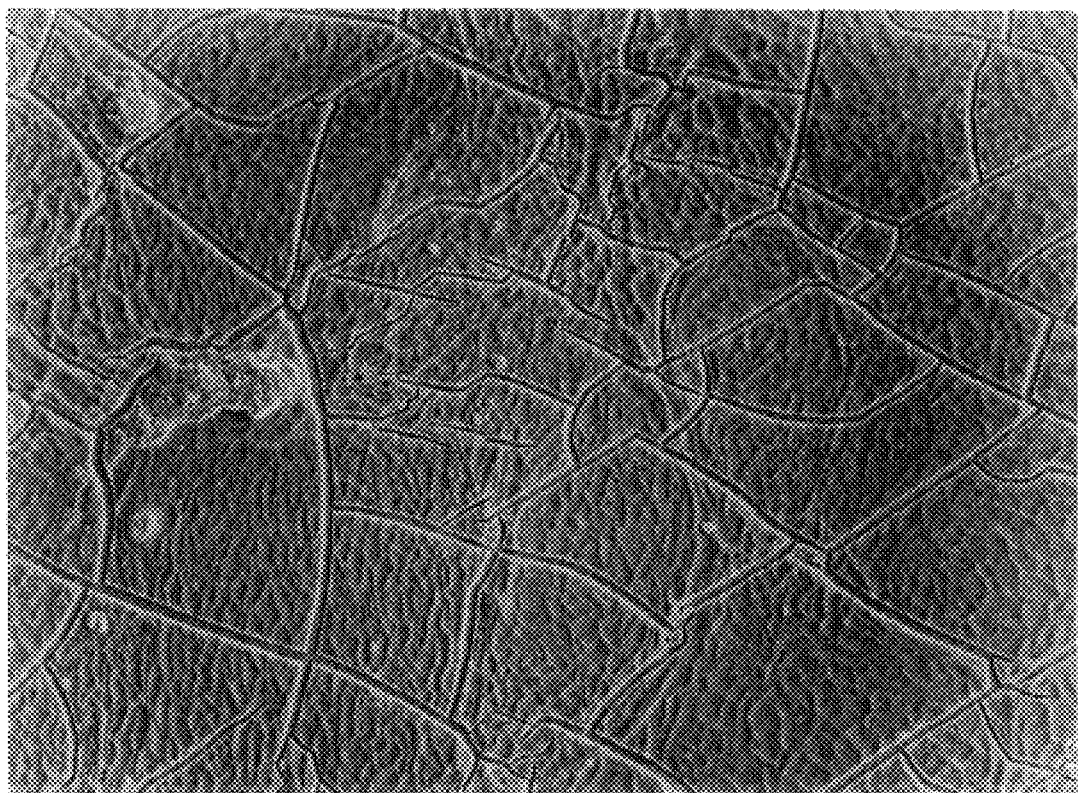
FIG. 3 is a SEM micrograph of the HAp of the HAp composite prepared in Example 5.

According to the present method discussed above, a HAp composite is obtained. The HAp in the composite includes crystalline HAp, of which crystals may be in the form of flakes, plates, or the like form. In particular, the present method enables formation of HAp having a novel structure with compact and layered crystals, for example, as shown in FIG. 3. The HAp in the composite is securely attached to the matrix.

The thickness of the HAp layer in the composite may suitably be selected depending on the kind and shape of the matrix, or on the usage of the composite. For example, the HAp layer of about 0.0001 to 5 mm thick is appropriate. The HAp composite may be made in a variety of shapes by suitably selecting the shape of the matrix, or by processing the HAp composite into a desired shape.

Accordingly, various kinds of biocompatible materials such as artificial bone may be produced with the HAp composite prepared by the present method, by suitably selecting the kind and shape of the matrix, or by processing the composite into a desired shape.

The biocompatible material of the present invention may optionally be subjected to a known sintering process, surface-treatment process, or the like process, depending on the usage.

According to the method for preparing a HAp composite of the present invention, since a matrix which has been made hydrophilic at least on its surface is used, and HAp is securely formed through the alternate soaking process, the HAp formed by the method is securely fixed on the matrix. Further, since the HAp is crystalline, a composite having the composition and structure similar to natural bone can be prepared quickly and easily. The composite prepared by this method is useful as various kinds of biocompatible materials such as artificial bone.

EXAMPLES

The present invention will now be explained in detail with reference to following Examples and Comparative Examples. However, the present invention is not limited to these.

Comparative Example 1

A 5×6 cm polyethylene (PE) film manufactured by SHOWA DENKO K.K. was used as a matrix. This matrix was soaked in 10 ml of a 200 mM $CaCl_2$/Tris-HCl solution (pH 7.4, solution temperature at 37° C.) for one minute, and subsequently in 10 ml of a 120 mM $Na_2HPO_4$ solution (solution temperature at 37° C.) for one minute. This cycle of alternate soaking operations was repeated 50 cycles, to thereby prepare a HAp composite. X-ray diffraction of the product with GEIGERFLEX 2013 (X-ray diffractometer manufactured by RIGAKU CO.) indicated that the product was HAp having characteristic peaks at 260° and 32°. Further, the amount of the HAp formed was measured. Also, in order to evaluate the bonding strength of the obtained HAp to the matrix, Cross Cut Exfoliation Test was conducted in accordance with ASTM D-2197 using Automatic Cross Cut Exfoliation Tester No. 551-B manufactured by YASUDA SEIKI SEISAKUSYO, LTD. The HAp composite showing a test result in the range of 90/100 to 100/100 was evaluated as "not peeled", whereas that showing a test result in the range of 90/100 or less was evaluated as "peeled". The results are shown in Table 1.

Example 1

Three pieces of 5×6 cm PE film manufactured by SHOWA DENKO K.K. were subjected to corona treatment at 15 kV for 2 minutes, 5 minutes, and 10 minutes, respectively, to obtain three kinds of PE film matrices that had been made hydrophilic on their surface. Each matrix was soaked in 10 ml of a 200 mM $CaCl_2$/Tris-HCl solution (pH 7.4, temperature at 37° C.) for one minute, washed with pure water on its surface, soaked in acetone, and air-dried. A series of these operations including the soaking of the matrix in the calcium ion aqueous solution is referred to as soaking operation (i). Subsequently, each matrix was soaked in 10 ml of a 120 mM $Na_2HPO_4$ solution (temperature at 37° C.) for one minute, washed with pure water on its surface, soaked in acetone, and air-dried. A series of these operations including the soaking of the matrix in the phosphate ion aqueous solution is referred to as soaking operation (ii).

A cycle of the alternate soaking process consisting of soaking operations (i) and (ii) was repeated 50 cycles for each matrix to form HAp composites. SEM (scattered electron microscope) micrographs of the products and X-ray diffraction of the products with GEIGERFLEX 2013 (X-ray diffractometer manufactured by RIGAKU CO.) indicated that all of the products were HAp having characteristic peaks at 26° and 32°, and mainly composed of crystalline HAp in the form of flakes The composites were subjected to the measurement of the HAp amount and the Exfoliation Test in the same way as in Comparative Example 1. The results are shown in Table 1.

Example 2

HAp was formed in the same way as in Example 1 except that the corona-treated PE film matrix was replaced with a PE film matrix that had been made hydrophilic on its surface by soaking PE film in sulfuric acid for 10 minutes for acid treatment. The resulting HAp composite was subjected to the measurement of the HAp amount and the Exfoliation Test in the same way as in Comparative Example 1. The results are shown in Table 1.

Example 3

HAp was formed in the same way as in Example 1 except that the corona-treated PE film matrix was replaced with a PE film matrix that had been made hydrophilic on its surface by rubbing PE film surface with a P400 file in two diagonal directions each for 50 times and in total of 100 times for surface-filing treatment. The resulting HAp composite was subjected to the measurement of the HAp amount and the Exfoliation Test in the same way as in Comparative Example 1. The results are shown in Table 1.

TABLE 1

| | Treatment of matrix surface | Amount of HAp formed | HAp Exfoliation Test |
|---|---|---|---|
| Comp. Ex. 1 | None | 2 $\mu g/cm^2$ | Peeled |
| Example 1 | Corona treatment for 2 min. | 3.9 $\mu g/cm^2$ | Not Peeled |
| | Corona treatment for 5 min. | 4.2 $\mu g/cm^2$ | Not Peeled |
| | Corona treatment for 10 min. | 5.1 $\mu g/cm^2$ | Not Peeled |
| Example 2 | Acid (Sulfuric acid) treatment | 2.7 $\mu g/cm^2$ | Not Peeled |
| Example 3 | Filing | 2.6 $\mu g/cm^2$ | Not Peeled |

Examples 4 and 5 and Comparative Example 2

Two PE film matrices that had been made hydrophilic on their surface by subjecting PE film to corona treatment for 2 minutes in Example 1 were provided. Each matrix was soaked in a 10 vol % aqueous solution of acrylic acid (AAc) (prepared by distilling under reduced pressure a guaranteed grade acrylic acid manufactured by WAKO PURE CHEMICAL INDUSTRIES, LTD.), to effect radical polymerization at 60° C., to thereby prepare two poly-AAc-grafted PE film matrices each having 23 $\mu g/cm^2$ of grafts (Example 4) and 43 $\mu g/cm^2$ of grafts (Example 5). A PE film matrix used in Comparative Example 1 was used as Comparative Example 2.

Next, each matrix was soaked in 10 ml of a 200 mM $CaCl_2$/Tris-HCl solution (pH 7.4, solution temperature at 37° C.) for one minute, washed with pure water on its surface; soaked in acetone, and air-dried. A series of these operations including the soaking of the matrix in the calcium ion aqueous solution is referred to as soaking operation (i). Subsequently, each matrix was soaked in 10 ml of a 120 mM $Na_2HPO_4$ solution (temperature at 37° C.) for one minute, washed with pure water on its surface, soaked in acetone, and air-dried. A series of these operations including the soaking of the matrix in the phosphate ion aqueous solution is referred to as soaking operation (ii).

Figure 2:
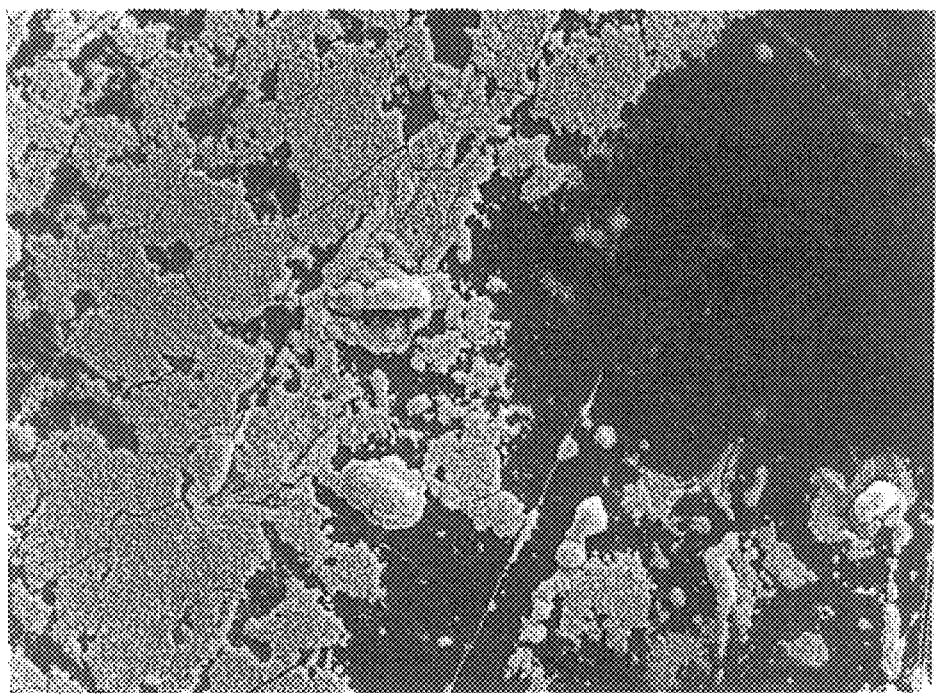
FIG. 2 is a SEM micrograph of the HAp of the HAp composite prepared in Example 4.

A cycle of the alternate soaking process consisting of soaking operations (i) and (ii) was repeated 50 cycles for each matrix to form HAp composites. SEM (scattered electron microscope) micrographs of the products and X-ray diffraction of the products with GEIGERFLEX 2013 (X-ray diffractometer manufactured by RIGAKU CO.) indicated that all of the products were HAp having characteristic peaks at 26° and 32°. The HAp of the composites obtained in Examples 4 and 5 had layered HAp crystals, and securely attached to the matrices. In particular, the HAp of the composite obtained in Example 5 had compact HAp crystals that had not been observed in conventional HAp. On the other hand, the HAp of the composite obtained in Comparative Example 2 had amorphous HAp and flake-like HAp crystals, and merely weakly attached to the matrix. SEM micrographs indicating these results are shown in FIGS. 1 to 3.

Example 6

Six PE film matrices that had been made hydrophilic on their surface by subjecting PE films to corona treatment for two minutes in Example 1 were provided. Each matrix was soaked in a 10 vol % aqueous solution of AAc, acrylamide (AAm), 2-hydroxyethyl methacrylate (HEMA), glycosylethyl methacrylate (GEMA), aminomethyl-p-styrene (AMPS), or sodium styrenesulfonate (NaSS), to effect radical polymerization at the temperature and for the duration as shown in Table 2, to thereby prepare six matrices.

Next, each matrix was subjected to 50 cycles of the alternate soaking process consisting of soaking operations (i) and (ii) to form HAp composites. The amount of HAp in the resulting composites was measured. The results are shown in Table 2.

TABLE 2

| Polymer material | Polymerization temperature | Duration of polymerization | Amount of HAp formed |
|---|---|---|---|
| AAc | 40° C. | 1 hr. | 6.2 $\mu g/cm^2$ |
| AAm | 40° C. | 1 hr. | 3.3 $\mu g/cm^2$ |
| HEMA | 60° C. | 24 hrs. | 2.1 $\mu g/cm^2$ |
| GEMA | 60° C. | 24 hrs. | 3.2 $\mu g/cm^2$ |
| AMPS | 60° C. | 24 hrs. | 3.3 $\mu g/cm^2$ |
| NaSS | 60° C. | 24 hrs. | 3.6 $\mu g/cm^2$ |

Comparative Example 3

A 5×6 cm stainless steel plate was used as a matrix. This matrix was soaked in 10 ml of a 200 mM $CaCl_2$/Tris-HCl solution (pH 7.4, solution temperature at 37° C.) for 2 hours, and excess moisture on the matrix surface was wiped off. Subsequently, the matrix was soaked in 10 ml of a 120 mM $Na_2HPO_4$ solution (solution temperature at 37° C.) for two hours, to thereby prepare a HAp composite. The HAp of the obtained composite was peeled off immediately.

Example 7

A stainless steel plate was soaked in sulfuric acid for 10 minutes to prepare an acid-treated matrix that had been made hydrophilic on its surface. A HAp composite was prepared in the same way as in Comparative Example 3 except that the acid-treated stainless steel matrix was used. The resulting HAp was not peeled off, and securely attached to the matrix, unlike the HAp obtained in Comparative Example 3, which was peeled off immediately. The amount of HAp formed was measured, and found to be 6.0 $\mu g/cm^2$.

Example 8

A stainless steel plate was rubbed on its surface with a P400 file in two diagonal directions each for 50 times and in total of 100 times to prepare a surface-filed matrix that had been made hydrophilic on its surface. A HAp composite was prepared in the same way as in Comparative Example 3 except that the surface-filed stainless steel matrix was used. The resulting HAp was not peeled off, and securely attached to the matrix, unlike the HAp obtained in Comparative Example 3, which was peeled off immediately. The amount of HAp formed was measured, and found to be 3.1 $\mu g/cm^2$.

Example 9

A titanium pin (manufactured by ETHICON INC.) was rubbed on the surface with a P400 file in two oblique directions each for 50 times and in total of 100 times to prepare a surface-filed matrix that had been made hydrophilic on its surface. A HAp composite was prepared in the same way as in Example 8 except that the surface-filed titanium pin matrix was used. The resulting HAp was not peeled off, and securely attached to the matrix, unlike the HAp obtained in Comparative Example 3, which was peeled off immediately.

The obtained HAp composite and an untreated titanium pin as a control were embedded in the peritoneum of a rat. After three days, the embedded HAp composite and the titanium pin were observed. It was found that the surface of the HAp composite was covered with the surrounding tissue, while the surface of the titanium pin was not. Subsequently, both were withdrawn from the peritoneum of the rat. The HAp composite was adhered to the surrounding tissue so that the withdrawal of the composite was accompanied by bleeding, whereas the titanium pin was easily withdrawn without any bleeding.

From the results above, it was demonstrated that the HAp composite of the present invention has superior biocompatibility, has HAp securely attached to the matrix, and is useful as a biomaterial.

Although the present invention has been described with reference to the preferred examples, it should be understood that various modifications and variations can be easily made by those skilled in the art without departing from the spirit of the invention.

Accordingly, the foregoing disclosure should be interpreted as illustrative only and is not to be interpreted in a limiting sense. The present invention is limited only by the scope of the following claims.

What is claimed is:

1. A method for preparing a hydroxyapatite composite comprising:
   alternately soaking a matrix which has been made hydrophilic at least on its surface in a calcium ion aqueous solution containing calcium ions and substantially free of phosphate ions and in a phosphate ion aqueous solution containing phosphate ions and substantially free of calcium ions to securely form hydroxyapatite at least on the surface of the said matrix.

2. The method of claim 1 wherein the said matrix which has been made hydrophilic at least on its surface has been prepared by a process selected from the group consisting of subjecting a polymer matrix to at least one of corona treatment, plasma treatment, acid treatment, base treatment, and surface-filing treatment, and subjecting a metal matrix to at least one of acid treatment on its surface, and a surface-filing treatment.

3. The method of claim 2 wherein the said polymer matrix is selected from the group consisting of polyurethane, polyethylene, polypropylene, poly(lactic acid), poly (glycolic acid), polyester, polyamide, polycarbonate, a fluoropolymer, a silicon elastomer, polyvinyl alcohol, polyethylene glycol, poly-γ-glutamic acid, collagen, glucosylethyl methacrylate (GEMA), partially sulfated GEMA, a mucopolysaccharide, cellulose, chitin, chitosan, pullulan and fibronectin.

4. The method of claim 2 wherein the said process of subjecting a polymer matrix to at least one of corona treatment, plasma treatment, acid treatment, base treatment, and surface-filing treatment is followed by graft-polymerization of a hydrophilic polymerizable compound to its surface.

5. The method of claim 4 wherein the said hydrophilic polymerizable compound has at least one of a carboxyl group, a phosphoric acid group, and a sulfonic acid group.

6. The method of claim 4 wherein the said hydrophilic polymerizable compound is selected from the group consisting of (meth)acrylic acid, alkyl ester of (meth)acrylic acid, alkylamide of (meth)acrylic acid, (meth)acrylic acid having a urethane bond, (meth)acrylic acid having a urea bond, (meth)acrylic acid having a phosphoric acid group, (meth) acrylic acid having a sulfonic acid group, and mixtures thereof.

7. The method of claim 2 wherein the said process of subjecting a polymer matrix to at least one of corona treatment, plasma treatment, acid treatment, base treatment, and surface-filing treatment is followed by reaction of a hydrophilic polymer with its surface.

8. The method of claim 7 wherein the said hydrophilic polymer has at least one of a carboxyl group, a phosphoric acid group, and a sulfonic acid group.

9. The method of claim 1 further comprising, after soaking the matrix which has been hydrophilic at least on its surface in the calcium ion aqueous solution containing calcium ions and substantially free of phosphate ions, removing the said calcium ion aqueous solution remaining on the matrix before soaking the matrix in the phosphate ion aqueous solution containing phosphate ions and substantially free of calcium ions.

10. The method of claim 9 wherein the said removing of the calcium ion aqueous solution containing calcium ions and substantially free of phosphate ions remaining on the matrix includes washing and drying the matrix.

11. The method of claim 1 further comprising, after soaking the matrix which has been made hydrophilic at least on its surface in the phosphate ion aqueous solution containing phosphate ions and substantially free of calcium ions, removing the said phosphate ion aqueous solution remaining on the matrix before soaking the matrix in the calcium ion aqueous solution containing calcium ions and substantially free of phosphate ions.

12. The method of claim 11 wherein the said removing of the phosphate ion aqueous solution containing phosphate ions and substantially free of calcium ions remaining on the matrix includes washing and drying the matrix.

* * * * *

UNITED STATES PATENT AND TRADEMARK OFFICE
CERTIFICATE OF CORRECTION

PATENT NO.   : 6,387,414 B1
DATED        : May 14, 2002
INVENTOR(S)  : Mitsuru Akashi et al.

It is certified that error appears in the above-identified patent and that said Letters Patent is hereby corrected as shown below:

<u>Title page,</u>
Item [75], Inventors, "Akio Hayashi", delete "Kashiwa" and substitute
-- Adachi-ku --; and delete "Kagoshima" and substitute -- Toyonaka-shi --.

Signed and Sealed this

Thirtieth Day of December, 2003

JAMES E. ROGAN
*Director of the United States Patent and Trademark Office*